(12) United States Patent
Grady et al.

(10) Patent No.: US 7,740,692 B2
(45) Date of Patent: Jun. 22, 2010

(54) WOOD PRESERVATIVE COMPOSITION

(75) Inventors: Robert W. Grady, Letart, WV (US); William C. Hoffman, Dunbar, WV (US); Stephen W. King, Scot Depot, WV (US)

(73) Assignee: Union Carbide Chemicals & Plastics Technology LLC

( * ) Notice: Subject to any disclaimer, the term of this patent is extended or adjusted under 35 U.S.C. 154(b) by 0 days.

(21) Appl. No.: 11/922,173

(22) PCT Filed: Jun. 7, 2006

(86) PCT No.: PCT/US2006/022395
§ 371 (c)(1),
(2), (4) Date: Jan. 6, 2009

(87) PCT Pub. No.: WO2007/005195
PCT Pub. Date: Jan. 11, 2007

(65) Prior Publication Data
US 2009/0211487 A1 Aug. 27, 2009

Related U.S. Application Data

(60) Provisional application No. 60/695,128, filed on Jun. 29, 2005.

(51) Int. Cl.
*A01N 33/02* (2006.01)
*A01N 33/12* (2006.01)
*A01N 59/16* (2006.01)
*A01N 59/20* (2006.01)
*B27K 3/52* (2006.01)

(52) U.S. Cl. .............. 106/18.32; 106/15.05; 106/18.35; 424/617; 424/638; 424/641; 514/642; 514/740

(58) Field of Classification Search .............. 106/15.05, 106/18.32, 18.35; 514/642, 740; 424/617, 424/638, 641
See application file for complete search history.

(56) References Cited

U.S. PATENT DOCUMENTS

| | | | |
|---|---|---|---|
| 4,622,248 A | 11/1986 | Leach et al. | |
| 4,761,179 A * | 8/1988 | Goettsche et al. | 106/18.32 |
| 4,857,322 A | 8/1989 | Goettsche et al. | |
| 4,871,473 A | 10/1989 | Goettsche et al. | |
| 5,049,677 A | 9/1991 | Prout et al. | |
| 5,118,699 A | 6/1992 | Willingham et al. | |
| 5,142,058 A | 8/1992 | Willingham et al. | |
| 5,145,981 A | 9/1992 | Willingham | |
| 5,186,947 A | 2/1993 | Goettsche et al. | |
| 5,187,194 A * | 2/1993 | Goettsche et al. | 514/499 |
| 5,210,094 A | 5/1993 | Reeve | |
| 5,342,836 A | 8/1994 | Reeve | |
| 5,725,806 A | 3/1998 | Ghosh | |
| 5,756,005 A | 5/1998 | Ghosh et al. | |
| 5,853,766 A * | 12/1998 | Goettsche et al. | 424/632 |
| 5,880,143 A * | 3/1999 | Goettsche et al. | 514/383 |
| 6,211,218 B1 * | 4/2001 | Goettsche et al. | 514/383 |
| 6,441,016 B2 * | 8/2002 | Goettsche et al. | 514/383 |
| 2002/0083864 A1 | 7/2002 | Higaki | |
| 2003/0010956 A1 | 1/2003 | Las et al. | |
| 2003/0031729 A1 | 2/2003 | Imai | |
| 2004/0258838 A1 | 12/2004 | Richardson et al. | |

FOREIGN PATENT DOCUMENTS

EP 425143 10/1996
EP 864406 9/1998

OTHER PUBLICATIONS

B. N. Barman and H. G. Preston, "The Effects of pH on the Degradation of Isothiazolone Biocides", Tribology International, (1992), 281-287.
Andrew Jacobson and Terry M. Williams, "The Environmental Fate of Isothiazolone Biocides", Chimica Oggi, Oct. 2000, 1-9.
Gary L. Willingham and Ronald L. Derbyshire, "Compatilbility and Stabilization of Methylchloro/Methyl-Isothiazolone in Metalworking Fluids", Lubrication Engineering, (1990), pp. 729-732, vol. 47.
Tirthankar Ghosh, "Reaction of Isothiazolones with Amines, Phosphorus, Sulfur and Silicon", (1999), pp. 367-368, vol. 153-154.
Giebeler, E. et al., "Fungicidal Water Soluble Wood Preservative—Containing Salt of 2-Hydroxy:Pyridine, Amino cpd. and Copper Salt", Derwent abstract, 1990-165019 of EP 370182, (May 1990).
Nagano Masahiro, et al., "Copper Based Wood Preserving Composition", Derwent Abstract, 2001-599694 of JP 2001-150404, (Jun. 2001).

* cited by examiner

*Primary Examiner*—Anthony J Green
(74) *Attorney, Agent, or Firm*—Paul D. Hayhurst

(57) ABSTRACT

A wood preservative composition resulting from admixing components comprising: at least one preservative metal; a quaternary ammonium compound; at least 2 amine compounds; a pH reducing agent, and water, wherein the pH of the composition is from about 7.1 to less than 8.5. Surprisingly, this combination of materials results in a stable solution that can contain a moldicide yet have a commercially acceptable shelf life.

7 Claims, No Drawings

WOOD PRESERVATIVE COMPOSITION

CROSS-REFERENCE TO PRIOR APPLICATION

This application is a 371 of PCT/US2006/022395 filed 7 Jun. 2006, which claims the benefit of U.S. Provisional Application Ser. No. 60/695,128, filed Jun. 29, 2005.

BACKGROUND OF THE INVENTION

The present invention relates to a method of preserving wood and a composition useful in that method.

The use of various compositions for the treatment and preservation of wood is well-known. For example, U.S. Pat. No. 4,622,248 describes the use of various metal compounds, acids, petroleum byproducts, fungicides and insecticides in wood preservative compositions. Wood preservative compositions containing complexes of copper and amines, and optional additives, are well known. For example, EP 0 864 406 A2 describes such a composition which comprises a moldicide. A popular class of wood preservative compositions are referred to as alkaline copper quat, or ACQ, solutions. The industrial standard for ACQ solutions is published by the American Wood Preservers' Association under standard P5-04 (Standard for Waterborne Preservatives).

Wood that is treated with copper-amine preservatives is susceptible to discoloration caused by fungus and mold. Retailers will not accept such discolored wood. Thus, wood treaters need to ensure that mold and fungus formation is prevented. That is why moldicides, such as 5-chloro-2-methyl-4-isothiazolin-3-one, are popular additives to copper-amine preservative solutions.

Unfortunately, popular isothiazolinone-based moldicides are unstable in ACQ solutions due to their alkalinity. Lowering the pH of the solution to improve the stability of isothiazolinone moldicides causes copper salts to precipitate, rendering the solution unsuitable for use. It would be desirable to have a copper-amine preservative for wood that would support such moldicides yet not suffer from copper salt precipitation.

SUMMARY OF THE INVENTION

The present invention is such a copper-amine wood preservative, and is a composition resulting from admixing components comprising: at least one preservative metal; a quaternary ammonium compound; at least 2 amine compounds; a pH reducing agent, and water, wherein the pH of the composition is from about 7.1 to less than 8.5. Surprisingly, this combination of materials results in a stable solution that can contain a moldicide yet have a commercially acceptable shelf life. In one embodiment, the invention is a composition resulting from admixing components comprising:

A. from about 0.5 to about 15 weight parts of a copper salt, a zinc salt or a mixture thereof;

B. from about 0.1 to about 10 weight parts of a quaternary ammonium compound;

C. an amount of a pH reducing agent that is sufficient to result in the composition having a pH of from about 7.1 to less than 8.5;

D. from about 0.1 to about 4 weight parts of triethanolamine;

E. from about 1 to about 40 weight parts of a primary amine, a secondary amine or a mixture thereof; and F. water;

wherein the sum of components A-F equals 100 weight parts, and wherein the composition has a pH of from about 7.1 to less than 8.5.

DETAILED DESCRIPTION OF THE INVENTION

The method of the present invention employs a quaternary ammonium compound, a preservative metal, a mixed amine, a pH reducing agent, and water. The method results in a solution that is useful for preserving wood. Depending on the amount of water employed, the solution is a concentrate that suitably is further diluted prior to use, or is a solution ready for use "as is."

For the purposes of the present invention, the term "preservative metal" means any source of preservative metal cations. Preservative metal cations are those cations which can be effectively employed in a wood preservative solution. It is contemplated that the preservative metal cations will be associated with or react with negatively charged species in the preservative concentrate and/or wood treating solution. Examples of the preservative metals suitable for use in this invention include copper, cobalt, cadmium, nickel and zinc. Copper can be incorporated into the system as copper metal, provided a suitable oxidizing agent such as air, hydrogen peroxide or nitric acid is present, or as a salt or compound such as, for example, copper oxide, copper carbonate, copper basic carbonate, copper sulfate, or copper hydroxide. When cobalt, cadmium, nickel or zinc are used they may be incorporated into the system as a metal compound or metal salt such as a metal oxide, metal hydroxide, metal carbonate, etc., or as the metal itself provided a suitable oxidizing agent is present. Metal compounds that normally are insoluble or have low solubility in water can be solubilized in the presence of ammonia and/or amines. Copper and zinc are the preferred metals, with copper being most preferred. Mixtures of preservative metals can be employed.

The preservative metal is employed in a biocidally effective amount. In one embodiment of the invention, from about 0.1 to about 15 weight parts of preservative metal cations are employed, based upon the total weight of the solution. The amount of preservative metal cations preferably is from about 0.5 to about 10 weight parts.

The pH reducing agent employed in the invention suitably is any material that lowers the pH of the composition. The pH reducing agent preferably is an acid, but acid salts can also be employed. The pH reducing agent can be organic or inorganic. Examples of the pH reducing agent include: carbon dioxide; inorganic acids such as hydrochloric acid, nitric acid, sulfuric acid, boric acid, and phosphoric acid; and organic acids such as carbonic acid, acetic acid, formic acid, oxalic acid, citric acid, propionic acid and other higher aliphatic or aromatic acids. In one embodiment of the invention the pH reducer is an aliphatic monocarboxylic acid having from 2 to about 6 carbon atoms. Additionally, the organic acids may have additional substitution or other functionalities. Mixtures of pH reducing agents can be employed. For example, combinations of two or more organic acids and/or the salts of such acids can be used in carrying out this invention. Examples of acid salts include ammonium carbonate and ammonium bicarbonate. Isomers of acids or mixtures of isomers are also usable within the scope of this invention.

The pH reducing agent is employed in an amount such that the pH of the composition of the invention is less than 8.5. In one embodiment of the invention, the pH of the composition of the invention is from about 4 to less than 8.5, and preferably is from about 7.1 to less than 8.5. In one embodiment of the invention, the pH is from about 7.8 8.4.

Quaternary ammonium compounds are well known in the art and many are commercially available. The quaternary ammonium compound can be represented by the general formula $(R^1R^2R^3R^4N^+)X^-$, where $R^1$ and $R^2$ are independently chosen from the group consisting of alkyl groups having 1 to 3 carbon atoms, $R^3$ is chosen from the group consisting of alkyl groups having 8 to 20 carbon atoms, $R^4$ is chosen from the group consisting of alkyl groups having 8 to 20 carbon atoms, aryl groups and aryl-substituted alkyl groups where the substituted alkyl groups have 1-3 carbon atoms, and $X^-$ is an anion. Examples of the quaternary ammonium compound include allyl dibenzyl ammonium chlorides and carbonates, didecyl dimethyl ammonium chloride and alkyl dimethyl benzyl ammonium chloride. For the purposes of the present invention, the quaternary ammonium compound is not an amine.

The quaternary ammonium compound advantageously is employed in a biocidally effective amount. In one embodiment of the invention, the ratio of the quaternary ammonium compound to the preservative metal cation ranges from about 0.003 to about 30, preferably from about 0.1 to about 5, and more preferably from about 0.5 to about 1.

At least 2 amines, also referred to as a mixed amine, are employed in the invention. Examples of amines include ammonia, alkanolamines, alkyleneamines, and simple amines including aliphatic amines, arylamines, and aralkyl amines. The mixed amine can comprise one or more polyamines. For the purposes of the present invention, the term "polyamine" refers to molecules that contain more than one amine functionality. The mixed amine may include ammonia and any combination of primary, secondary and tertiary amines. Examples of amines include alkylamines, alkanolamines, and alkyleneamines. In one embodiment of the invention, the preferred mixed amine is a mixture of monoethanolamine and triethanolamine.

The mixed amine is employed in an amount effective to increase the solubility of the preservative metal in the solution. When 2 amines are employed, the ratio of the amines is not particularly critical and can range from about 5:1 to about 25:1 by weight. In one embodiment of the invention, the ratio of monoethanolamine to triethanolamine is from about 8:1 to about 12:1. The amount of mixed amine can be from about 1 to about 40 weight percent, based on the weight of the solution. In the case of a concentrate, the amount of mixed amine is preferably from about 15 to about 30 weight percent, based on the weight of the concentrate.

The amount of water is not particularly critical, and suitably is enough to solubilize the other components of the wood treating formulation, whether in concentrated or final form. In one embodiment of the invention, the amount of water can be from about 10 to about 90 weight percent based on the weight of the solution. The water employed in the composition of the invention can be added entirely in the form of one or more solutions of other components of the composition, such that no "water-only" component is employed.

One or more of various other additives may be added to the formulation if desired. Examples of optional additives include colorants, water repellants, UV absorbers, dimensional stabilizers, and organic co-biocides, including moldicides. Many types of these materials are commercially available and are well known in the art. Two moldicides commonly employed for wood treating applications include 5-chloro-2-methyl-4-isothiazalin-3-one (CMI) and 2-methyl-4-isothiazolin-3-one (MI).

The preservative is prepared by admixing the components under conditions such that a solution is obtained. In one embodiment of the invention, an aqueous mixed amine and the preservative metal are contacted under conditions such that a solution is obtained. The pH reducing agent is then added to the solution under conditions such that a solution is maintained. The quaternary ammonium compound and any optional additives are then added. It is also permissible to contact the components in different orders, so long as a solution results. The composition of the invention can be prepared as a concentrated solution, or concentrate, suitable for further dilution at a formulation facility or even a job site where the solution is to be applied to wood to be preserved. In another embodiment of the invention, the composition is prepared in a concentration that is ready for use as is. For typical concentrations, see the industrial standard for ACQ solutions, published by the American Wood Preservers' Association under standard P5-04 (Standard for Waterborne Preservatives), which is incorporated herein by reference.

The preservative solution may be formulated over a broad temperature range, although the preferred temperature is between about 15° to 30° C. The limiting factors for selecting a suitable temperature are the freezing point of the preservative and the loss of ammonia at high temperature due to evaporation. Such ammonia loss may be controlled by maintaining the system under suitable pressure.

The amount and concentration of treating solution applied to a particular substrate will depend upon many factors well-known to those skilled in the art, such as the nature of the substrate (species of wood), its end use, its geographic location, the method of application and the nature of the attack to be prevented. A preservative is usually applied to a substrate in a quantity sufficient to produce a desired preservative end point and thus, actual quantities may vary widely. In preparing these solutions for application to a substrate, a concentrated stock solution commonly is first made, or is obtained as a commercial preparation, and is thereafter diluted to a final working solution having the desired concentration.

The desired level of preservative retention will likewise depend on several factors known to those skilled in the art such as method of application, geographic location, species of wood, etc.

The treating solution may be applied to wood by dipping, soaking, spraying, brushing, or any other well known means. Vacuum and/or pressure techniques may also be used to impregnate the wood in accord with this invention including both the "Empty Cell" process and the "Full Cell" process, both of which are well known to those skilled in the art.

Before impregnating timber with any wood treating solution it is essential to season it first until at least all the free water has been removed from the cell spaces. This stage of seasoning represents a moisture content of about 25%-30%, varying slightly with different species. There are two very good reasons for this: firstly, it is not possible to inject another liquid into wood containing too much water, and secondly, splits developing as the result of the subsequent drying of the timber would almost certainly expose untreated timber. It is also desirable to carry out all cutting, machining and boring, etc., of the timber before treatment is applied, as all these operations, if carried out after treatment, would expose untreated wood. Where these operations cannot be done until after treatment, all exposed untreated timber should be given a liberal application of treating solution, and holes preferably should be treated with a pressure bolt-hole treater.

SPECIFIC EMBODIMENTS OF THE INVENTION

The following examples are given to illustrate the invention and should not be construed as limiting its scope. All parts and percentages are by weight unless otherwise indicated.

Example 1

In this Example, a commercially available NATURE-WOOD brand ACQ treating solution (hereinafter ACQ-1), (available from Osmose, Inc., Buffalo, N.Y., 1 percent active ingredients) is employed neat, and as modified to contain 0.1, 0.2, 0.4, and 0.6% (weight) of triethanolamine (TEA). A Material Safety Data Sheet last revised Apr. 10, 2002 indicates that ACQ-1 includes monoethanolamine, a copper-containing complex, a quaternary ammonium chloride, and other components. Acetic acid is added to 20 mL samples of each solution with shaking until the solution becomes turbid. The pH at which turbidity first persists while the sample is shaken is recorded for each sample and shown in Table 1.

TABLE 1

Effect of TEA Concentration on Precipitation pH of Copper Salts

| TEA (wt %) | Turbidity pH |
| --- | --- |
| 0 | 8.2 |
| 0.1 | 8.1 |
| 0.2 | 7.8 |
| 0.4 | 7.5 |
| 0.6 | 6.8 |

This example shows that the addition of TEA lowers the pH at which turbidity first appears. Turbidity indicates that precipitates will form when the sample is allowed to stand. The relative amount of TEA in the sample determines how low the pH can be adjusted before evidence of precipitation occurs.

Example 2

Three samples are prepared using ACQ-1 as the starting material. For the first sample, ACQ-1 is adjusted to pH 8.0 with acetic acid. To another sample of ACQ-1 is added 2000 ppm TEA, and the pH is then adjusted to 7.8 with acetic acid. The third sample is prepared by adding 2000 ppm TEA to ACQ-1 and adjusting the pH to 7.6 with acetic acid. A precipitate is visible in the first and third samples, but not in the second (ACQ-1+2000 ppm TEA, pH 7.8).

What is claimed is:

1. A composition resulting from admixing components comprising: at least one preservative metal; a quaternary ammonium compound; at least 2 amine compounds; and a pH reducing agent, and water, wherein the pH of the composition is from about 7.1 to less than 8.5, wherein the pH reducing agent comprises an aliphatic monocarboxylic acid having from 2 to 6 carbon atoms, and wherein the amine compounds comprise monoethanolamine and triethanolamine.

2. The composition of claim 1, wherein the concentration of the amine compounds is from about 1 to about 40 wt %, based on the weight of the composition.

3. The composition of claim 1, wherein pH reducing agent comprises at least one of oxalic acid or citric acid.

4. The composition of claim 1 wherein the quaternary ammonium compound is represented by the general formula $(R^1R^2R^3R^4N^+)X^-$, where $R^1$ and $R^2$ are independently chosen from the group consisting of alkyl groups having 1 to 3 carbon atoms, $R^3$ is chosen from the group consisting of alkyl groups having 8 to 20 carbon atoms, $R^4$ is chosen from the group consisting of alkyl groups having 8 to 20 carbon atoms, aryl groups and aryl-substituted alkyl groups where the substituted alkyl groups have 1-3 carbon atoms, and $X^-$ is an anion.

5. The composition of claim 1, wherein the pH is from about 7.8 to less than about 8.5.

6. The composition of claim 1 wherein a biocidally effective amount of at least one quaternary ammonium compound is employed, the preservative metal is a biocidally effective amount of at least one salt of copper or zinc, and wherein a ratio of the quaternary ammonium compound to a cation of the copper or zinc salt ranges from about 0.003 to about 30.

7. A composition resulting from admixing components comprising:
   A. from about 0.5 to about 15 weight parts of a copper salt, a zinc salt or a mixture thereof;
   B. from about 0.1 to about 10 weight parts of a quaternary ammonium compound;
   C. an amount of a pH reducing agent that is sufficient to result in the composition having a pH of from about 7.1 to less than 8.5, wherein the pH reducing agent comprises at least one of oxalic acid or citric acid;
   D. from about 0.1 to about 4 weight parts of triethanolamine;
   E. from about 1 to about 40 weight parts of monoethanolamine; and
   F. water;
   wherein the sum of components A-F equals 100 weight parts, and wherein the composition has a pH of from about 7.1 to less than 8.5.

* * * * *